US 9,999,390 B2

(12) United States Patent
Yao et al.

(10) Patent No.: US 9,999,390 B2
(45) Date of Patent: Jun. 19, 2018

(54) METHOD AND SYSTEM FOR MEASURING UREA

(71) Applicant: Verily Life Sciences LLC, Mountain View, CA (US)

(72) Inventors: Huanfen Yao, Sunnyvale, CA (US); Zenghe Liu, Alameda, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1184 days.

(21) Appl. No.: 14/056,872

(22) Filed: Oct. 17, 2013

(65) Prior Publication Data

US 2015/0112175 A1 Apr. 23, 2015

(51) Int. Cl.
  *A61B 5/05* (2006.01)
  *A61B 5/00* (2006.01)
  *A61B 5/145* (2006.01)
  *A61B 5/1486* (2006.01)
  *A61B 5/1477* (2006.01)

(52) U.S. Cl.
  CPC .......... *A61B 5/6821* (2013.01); *A61B 5/0004* (2013.01); *A61B 5/1477* (2013.01); *A61B 5/1486* (2013.01); *A61B 5/14507* (2013.01); *A61B 5/14546* (2013.01); *A61B 5/6803* (2013.01)

(58) Field of Classification Search
  CPC ......... A61B 5/00; A61B 5/145; A61B 5/1486; A61B 5/6821; A61B 5/0004; A61B 5/14507; A61B 5/1477; A61B 5/14546; A61B 5/6803
  See application file for complete search history.

(56) References Cited

U.S. PATENT DOCUMENTS

| 5,858,186 A * | 1/1999 | Glass ..................... C12Q 1/005 204/403.14 |
| 7,809,417 B2 | 10/2010 | Abreu |
| 8,096,654 B2 | 1/2012 | Amirparviz et al. |
| 2002/0049374 A1 | 4/2002 | Abreu |
| 2002/0049389 A1 | 4/2002 | Abreu |
| 2010/0227345 A1 | 9/2010 | LeJuene et al. |
| 2012/0245444 A1* | 9/2012 | Otis ..................... A61B 5/1486 600/345 |

(Continued)

OTHER PUBLICATIONS

Ali, et al. "Selective determination of urea using urease immobilized on ZnO nanowires," Sensors and Actuators B: Chemical, vol. 160, Issue 1, Dec. 15, 2011, pp. 637-643.*

(Continued)

*Primary Examiner* — Navin Natnithithadha
*Assistant Examiner* — Eric Messersmith
(74) *Attorney, Agent, or Firm* — McDonnell Boehnen Hulbert & Berghoff LLP

(57) ABSTRACT

A body-mountable urea sensing device includes an electrochemical sensor embedded in a polymeric material configured for mounting to a surface of an eye. The electrochemical sensor includes a working electrode, a reference electrode, and a reagent localized near the working electrode that selectively reacts with urea. A potentiometric voltage between the working electrode and the reference electrode is related to a concentration of urea in a fluid to which the electrochemical sensor is exposed; the voltage is measured by the body-mountable device and wirelessly communicated.

19 Claims, 9 Drawing Sheets

(56) References Cited

U.S. PATENT DOCUMENTS

2012/0259188 A1   10/2012   Besling
2013/0102921 A1   4/2013   Saurer et al.
2013/0135578 A1   5/2013   Pugh et al.

OTHER PUBLICATIONS

Syed Usman Ali et al., "Selective determination of urea using urease immobilized on ZnO nanowires," Sensors and Actuators B: Chemical, vol. 160, pp. 637-643 (2011).
Gavrilov et al., "Tear/Plasma Urea Ration as a Correction Coefficient for Drug Monitoring in Tears," J. Pharm. Technol., 2000, pp. 18-20, vol. 16.
Zapata et al., "Tear urea nitrogen and creatinine levels in horse and their correlation with serum values," Veterinary Ophthalmology, 2005, pp. 207-209, vol. 8, No. 3.
International Search Report and Written Opinion for PCT/US2014/059708 dated Jan. 28, 2015, 19 pages.

* cited by examiner

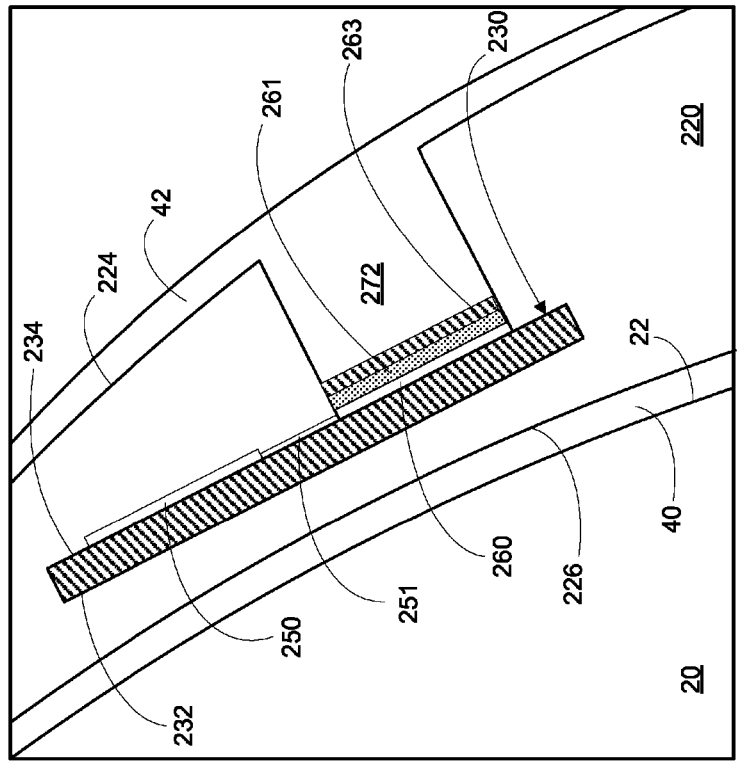
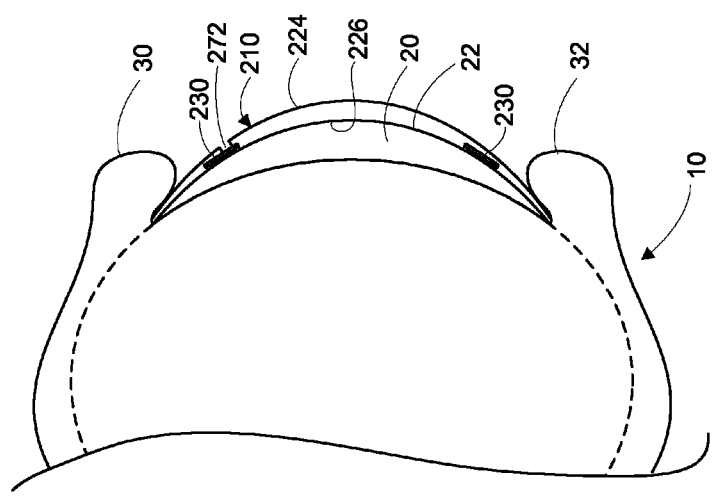
FIG. 2D
FIG. 2C

METHOD AND SYSTEM FOR MEASURING UREA

BACKGROUND

Unless otherwise indicated herein, the materials described in this section are not prior art to the claims in this application and are not admitted to be prior art by inclusion in this section.

Electrochemical potentiometric sensors measure concentrations of an analyte by measuring voltage differences that develop between two or more electrodes exposed to a solution containing one or more analytes. One of the two more electrodes is a reference electrode that has a known potential in the solution that is substantially unchanged by changes in concentration of the one or more analytes. Another of the two or more electrodes is a working electrode whose potential in the solution is selectively changed by changes in concentration of the one or more analytes. Substantially no current is allowed to flow through the reference and working electrodes. The voltage difference between the reference electrode and the working electrode is thus related to the concentration of the one or more analytes in the solution. Measurement of the voltage between the reference electrode and the working electrode can be performed by a high-impedance voltmeter.

SUMMARY

Some embodiments of the present disclosure provide a body-mountable device including: a shaped polymeric material; a substrate at least partially embedded within the shaped polymeric material; an antenna disposed on the substrate; an electrochemical sensor disposed on the substrate and comprising: a working electrode, a reagent that selectively reacts with urea localized proximate to the working electrode, and a reference electrode; and a controller electrically connected to the electrochemical sensor and the antenna. The controller can be configured to: (i) measure a potentiometric voltage between the working electrode and the reference electrode related to the concentration of urea in a fluid to which the body-mountable device is exposed; and (iii) use the antenna to indicate the measured potentiometric voltage.

Some embodiments of the present disclosure provide a method including: exposing a working electrode and a reference electrode to a fluid, wherein the working electrode and reference electrode are disposed in a body-mountable device, wherein the working electrode is selectively sensitive to urea, wherein the body-mountable device additionally includes an antenna and measurement electronics, and wherein the working electrode, reference electrode, antenna, and measurement electronics are disposed on a substrate that is at least partially embedded in a shaped polymeric material; measuring a voltage between the working electrode and the reference electrode related to the concentration of urea in the fluid to which the body-mountable device is exposed; and wirelessly indicating the measured voltage using an antenna which is also disposed in the body-mountable device.

Some embodiments of the present disclosure provide a system comprising: an antenna configured to wirelessly communicate with a body-mountable device, wherein the body-mountable device is configured to measure a voltage related to the concentration of urea in a fluid to which the body-mountable device is exposed; a processor; user controls; and a non-transitory computer readable medium containing instructions that can be executed by the processor to cause the system to perform functions including: (i) using the radio frequency antenna to interrogate the body-mountable device by transmitting a radio frequency signal, (ii) receiving from the body-mountable device a radio-frequency signal indicating a measured voltage, (iii) determining a urea concentration in the fluid based on the indicated measured voltage.

Some embodiments of the present disclosure provide a method including: interrogating a body-mountable device, the body-mountable device including an antenna, measurement electronics, and an electrochemical sensor with a working electrode and a reference electrode, wherein a reagent that selectively reacts with urea is localized proximate to the working electrode, wherein the antenna, measurement electronics, and the electrochemical sensor are disposed on a substrate that is at least partially embedded in a shaped polymeric material, by transmitting radio frequency radiation sufficient to power the electrochemical sensor and measurement electronics to measure a voltage difference between the working electrode and the reference electrode related to urea; receiving, from the body-mountable device, a radio frequency signal indicating the measured voltage; and determining a concentration of urea based on the measured voltage indicated by the radio frequency signal.

Some embodiments of the present disclosure provide a method including: forming a substrate; disposing components on the substrate, wherein the components include an electrochemical sensor having at least a working electrode and a reference electrode, measurement electronics, and a radio frequency antenna; at least partially embedding the substrate and components disposed thereon in a shaped polymeric material; and localizing a reagent that reacts selectively with urea proximate to the working electrode.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2C is a side cross-section view of the example eye-mountable device shown in FIGS. 2A and 2B while mounted to a corneal surface of an eye.

FIG. 2D is a side cross-section view enhanced to show the tear film layers surrounding the surfaces of the example eye-mountable device when mounted as shown in FIG. 2C.

DETAILED DESCRIPTION

Figure 1:
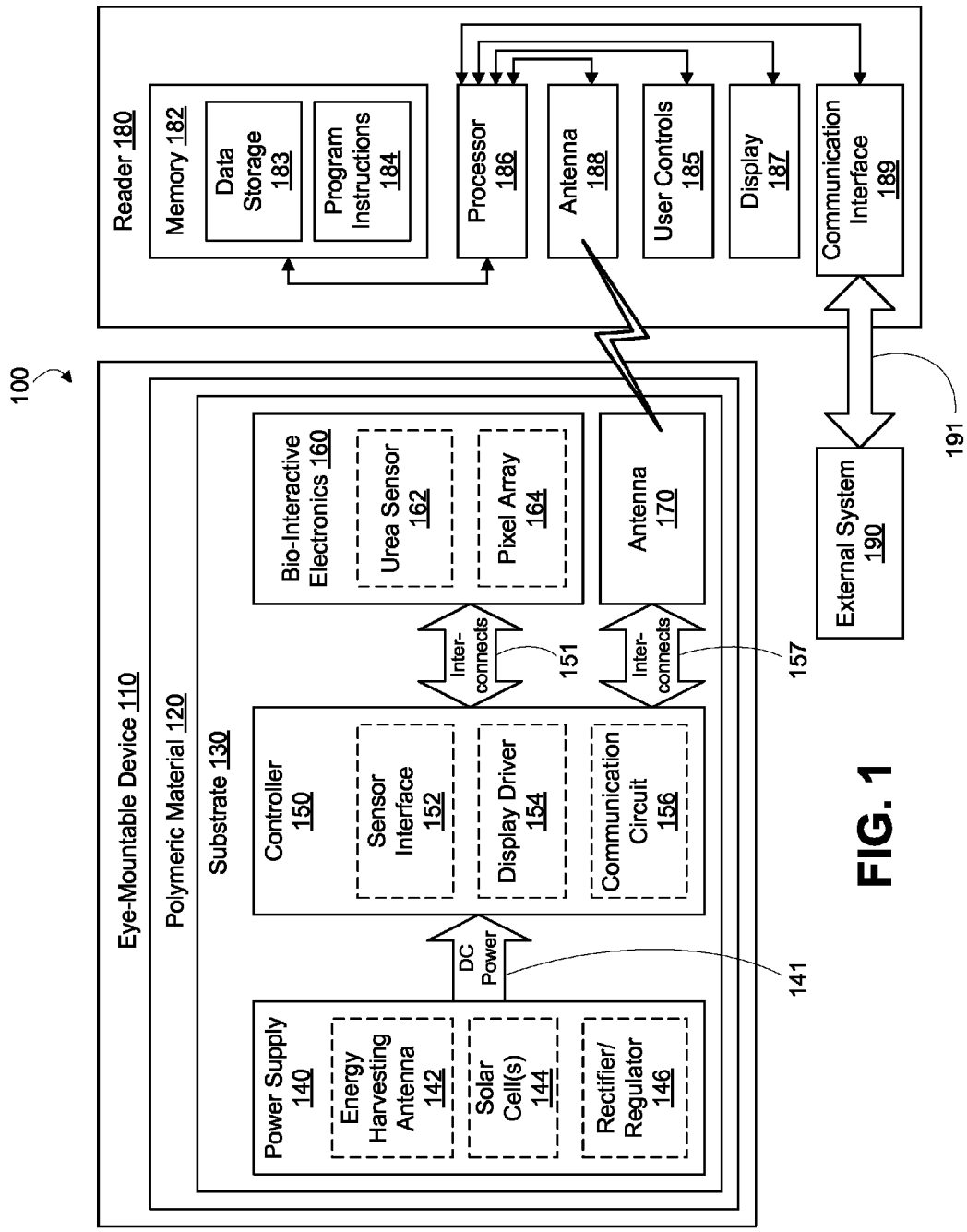
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Some embodiments of the present disclosure provide an eye-mountable device configured to rest on corneal tissue, such as a contact lens, with one or more electrochemical sensors for quantitatively and qualitatively testing urea concentration in a tear film in situ and in real-time. Those of skill in the art will recognize that the sensing platform described herein may be provided in devices that could be mounted on portions of the human body other than the eye to measure concentrations of urea in other fluids than a tear film of an eye. Those of skill in the art will also recognize that the sensing platform described herein may be provided in devices that could be mounted in locations other than locations on the human body to measure concentrations of urea in a fluid proximate to the mounting location of the devices.

An ophthalmic sensing platform can include an electrochemical sensor, control electronics and an antenna all situated on a substrate embedded in a polymeric material formed to be contact mounted to an eye. The control electronics can operate the sensor to perform measurements of urea concentration and can operate the antenna to wirelessly communicate the measurements from the sensor to an external reader via the antenna.

In some examples, the polymeric material can be in the form of a round lens with a concave curvature configured to mount to a corneal surface of an eye. The substrate can be embedded near the periphery of the polymeric material to avoid interference with incident light received closer to the central region of the cornea. The sensor can be arranged on the substrate to face inward, toward the corneal surface so as to generate clinically relevant readings from near the surface of the cornea and/or from tear fluid interposed between the contact lens and the corneal surface. Additionally or alternatively, the sensor can be arranged on the substrate to face outward, away from the corneal surface and toward the layer of tear fluid coating the surface of the polymeric material exposed to the atmosphere. In some examples, the sensor is entirely embedded within the contact lens material. For example, the sensor can be suspended in the lens material and situated such that the working electrode is less than 10 micrometers from the polymeric surface configured to mount to the cornea. The sensor can generate an output signal indicative of a concentration of an analyte that diffuses through the lens material to the embedded sensor. In some examples, the sensor is directly exposed to the analyte-containing fluid. For example, the lens material can be formed such that a there is a window in the lens material over the sensor, allowing the analyte-containing fluid to directly contact the sensor. In another example, a channel is formed in the lens material from the surface of the lens material to the sensor, allowing the analyte-containing fluid to fill the channel. In this example, the sensor can generate an output signal indicative of a concentration of an analyte in the fluid in the channel.

In some examples, the electrochemical sensor disposed in the ophthalmic sensing platform can include a working electrode sensitive to urea and a reference electrode. By exposing the sensing platform to a target fluid, a potentiometric voltage is developed that can indicate the concentration of urea near the working electrode. The working electrode can be made sensitive to urea by localizing a reagent selectively reactive with urea near a working electrode of the sensor. In some examples, the enzyme urease can be deposited onto particles of a pH-sensitive oxide nano-powder that is disposed on the working electrode. In those examples, the urease selectively reacts with urea, creating products including ammonia. The ammonia then interacts with the working electrode, resulting in a voltage that can be related to the concentration of urea near the working electrode.

The ophthalmic sensing platform can be powered via one or more batteries in the sensing platform or by energy from an external source. For example, power can be provided by light energizing photovoltaic cells included on the sensing platform. Additionally or alternatively, power can be provided by radio frequency energy harvested from the antenna. A rectifier and/or regulator can be incorporated with the control electronics to generate a stable DC voltage to power the sensing platform from the harvested energy. The antenna can be arranged as a loop of conductive material with leads connected to the control electronics. In some embodiments, such a loop antenna can wirelessly also communicate the sensor readings to an external reader by modifying the impedance of the loop antenna so as to modify backscatter radiation from the antenna.

In some examples, an external reader can radiate radio frequency radiation to power the ophthalmic sensing platform via the energy harvesting system. The external reader may thereby control the operation of the sensing platform by controlling the supply of power to the sensing platform. In some examples, the external reader can operate to intermittently interrogate the sensing platform to provide a reading by radiating sufficient radiation to power the sensing platform to obtain a measurement and communicate the result. The external reader can also store the sensor results communicated by the sensing platform. In this way, the external reader can acquire a series of urea concentration measurements over time without continuously powering the sensing platform.

The external reader may be provided as a mobile device with software applications for displaying the sensor results. The external reader may also include a communications interface that can be configured to convey the measured urea concentrations to other systems for display, data storage, and/or analysis.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photo-resists, masks, deposition techniques and/or plating techniques can be employed to pattern materials on the substrate 130. The substrate 130 can be a relatively rigid material, such as polyethylene terephthalate ("PET"), parylene, or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in the center region of the eye-mountable device 110. The bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an electrochemical urea sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate electrochemical urea sensor 162. The electrochemical urea sensor 162 can be, for example, a potentiometric sensor that includes a working electrode and a reference electrode. A voltage can develop between the working and reference electrodes in response to a concentration of an analyte in a fluid to which the working electrode is exposed. Thus, the magnitude of the potentiometric voltage that is measured between the working electrode and the reference electrode can provide an indication of analyte concentration. In some embodiments, the sensor interface module 152 can be a high-impedance voltmeter configured to measure the voltage difference between working and reference electrodes while substantially preventing the flow of current through the working and reference electrodes.

In some instances, a reagent can also be included to sensitize the electrochemical sensor to urea. In one example, urease localized proximate to the working electrode can catalyze urea into ammonium ($NH_4^+$) and ammonium hydroxide ($NH_4OH$). The ammonium hydroxide can cause an increase in pH near the working electrode. The increase in pH can then be detected by a pH-responsive working electrode, resulting in an equilibrium potentiometric voltage that can be measured between the working electrode and the reference electrode.

$$\text{urea} + 3H_2O \xrightarrow{\text{urease}} 2NH_4^+ + HCO_3^- + OH^-$$

The equilibrium voltage in an example potentiometric electrochemical urea sensor is related to the concentration of urea near the working electrode. The relationship between voltage and concentration can be determined experimentally for individual electrochemical urea sensors or determined once for an example sensor or sensors and the calibration from the example sensor or sensors can be applied to other electrochemical urea sensors.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivably by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or group of more than one antennae) to send and receive wireless signals 171 to and from the eye-mountable device 110. The external reader 180 also includes a computing system with a processor 186 in communication with a memory 182. The external reader 180 can also include one or more of user controls 185, a display 187, and a communication interface 189. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the electrochemical urea sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to perform any of the function described herein. For example, program instructions 184 may cause the external reader 180 to provide a user interface that allows for retrieving information communicated from the eye-mountable device 110 (e.g., sensor outputs from the electrochemical urea sensor 162) by displaying that information on the display 187 in response to commands input through the user controls 185. The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can also be configured include a communication interface 189 to communicate signals via a communication medium 191 to and from a remote system 190. For example, the remote system 190 may be a smart phone, tablet computer, laptop computer, or personal computer, and communication interface 189 and communication medium 191 may be a Bluetooth module and wireless Bluetooth communication signals, respectively. In this example, the external reader 180 may be configured to send urea concentration data collected by the biosensor 160 to the smart phone, tablet computer, laptop computer, or personal computer for storage and offline analysis. In another example, the remote system 190 is a server at a clinic or physician's office, the communication interface 189 is a WiFi radio module, and the communication medium 191 is elements of the internet sufficient to enable the transfer of data between the remote server and the WiFi radio module. A physician may use this data to make determinations or diagnoses related to the subject's condition. Further, the external reader 180 may be configured to receive signals from a remote server, such as instructions sent by a physician at a remote location to, for example, increase or decrease sampling frequency. Communication interface 189 could be configured to enable other forms of wired or wireless communication; for example, CDMA, EVDO, GSM/GPRS, WiMAX, LTE, infrared, ZigBee, Ethernet, USB, FireWire, a wired serial link, or near field communication.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing worn near the head, such as a hat, headband, etc. The external reader 180 could also be implemented in eye glasses or a head-mounted display.

In an example where the eye-mountable device 110 includes an electrochemical urea sensor 162, the system 100 can be operated to measure the urea concentration in a tear film on the surface of the eye. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes urea, glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of urea can be established (e.g., empirically determined) to be approximately one tenth the corresponding blood urea concentration. Thus, measuring tear film yrea concentration levels provides a non-invasive technique for monitoring urea levels in comparison to blood sampling techniques performed by lancing a volume of blood to be analyzed outside a person's body. Moreover, the ophthalmic urea bio-sensor platform disclosed here can be operated substantially continuously to enable real time measurement of urea concentrations.

To perform a reading with the system 100 configured as a tear film urea sensor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus powers the electronic components within the eye-mountable device 110. Once powered, the controller 150 operates the urea sensor 162 to measure a urea concentration level. For example, the sensor interface module 152 can measure the voltage between a working electrode and a reference electrode in the urea sensor 162. The measured potentiometric voltage can provide the sensor reading ("result") indicative of the urea concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film urea concentration measurement and communicate the results. For example, the supplied radio frequency radiation can provide sufficient power to measure the potentiometric voltage between the working and reference electrodes and modulate the antenna impedance to adjust the backscatter radiation in a manner indicative of the measured potentiometric voltage. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

In other embodiments, the system 100 can operate continuously and supply energy to the eye-mountable device 110 to power the controller 150 and electronics 160 at all times. In some instances, it may be desirable to continuously measure urea concentration and collect, store, and or transmit this data.

Figure 2A:
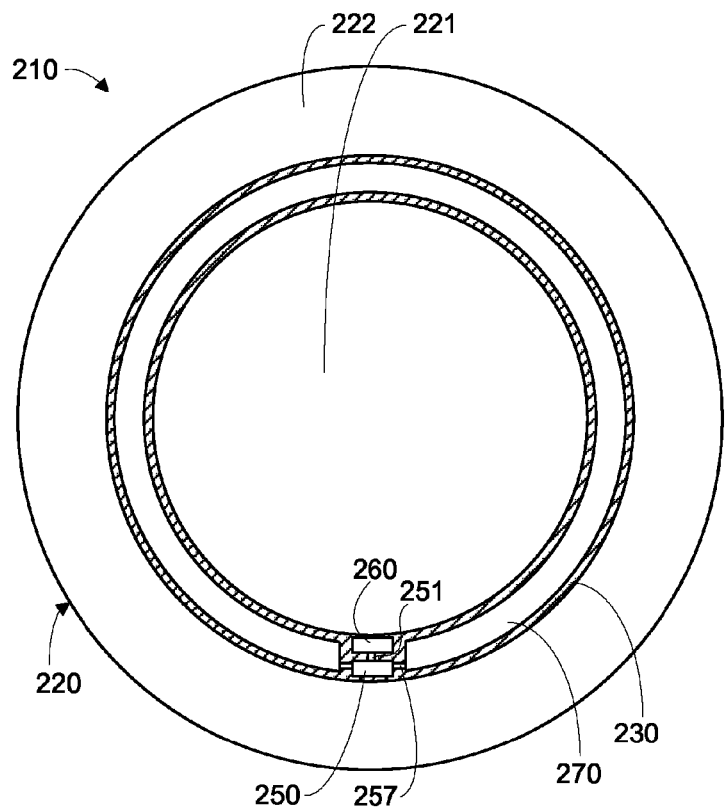
FIG. 2A is a bottom view of an example eye-mountable device.
Figure 2B:
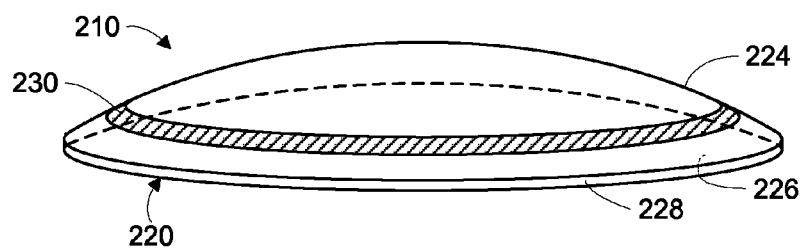
FIG. 2B is an aspect view of the example eye-mountable device shown in FIG. 2A.

FIG. 2A is a bottom view of an example eye-mountable electronic device 210. FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), silicone hydrogels, combinations of these, etc. The polymeric material 220 can be formed with one side having a concave surface 226 suitable to fit over a corneal surface of an eye. The opposing side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved out of the page, whereas the center region 221, near the center of the disk is curved in to the page.

A substrate 230 is embedded in the polymeric material 220. The substrate 230 can be embedded to be situated along the outer periphery 222 of the polymeric material 220, away from the center region 221. The substrate 230 does not interfere with vision because it is too close to the eye to be in focus and is positioned away from the center region 221 where incident light is transmitted to the eye-sensing portions of the eye. Moreover, the substrate 230 can be formed of a transparent material to further mitigate any effects on visual perception.

The substrate 230 can be shaped as a flat, circular ring (e.g., a disk with a central hole). The flat surface of the substrate 230 (e.g., along the radial width) is a platform for mounting electronics such as chips (e.g., via flip-chip mounting) and for patterning conductive materials (e.g., via deposition techniques) to form electrodes, antenna(e), and/or connections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical urea sensor, etc.) can be formed from conductive materials patterned on the substrate 230 by a process for precisely patterning such materials, such as deposition, lithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the concave surface 226 of the eye-mountable device 210, the bio-interactive electronics module 260 is mounted to a side of the substrate 230 facing the concave surface 226. Where the bio-interactive electronics module 260 includes a urea sensor, for example, mounting such a sensor on the substrate 230 to be close to the concave surface 226 allows the sensor to sense urea concentrations in tear film near the surface of the eye. However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made via conductive materials passing through the substrate 230.

The loop antenna 270 can be a layer of conductive material patterned along the flat surface of the substrate to form a flat conductive ring. In some instances, the loop antenna 270 can be formed without making a complete loop. For instance, the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can be passed through the substrate 230 to the controller 250.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the concave surface 226. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the outward-facing surface 234 such that the bio-interactive electronics 260 are relatively closer in proximity to the outer tear film layer 42 than if they were mounted on the inward-facing surface 232. With this arrangement, the bio-interactive electronics 260 can receive urea concentrations in the outer tear film 42 through the channel 272. However, in other examples, the bio-interactive electronics 260 may be mounted on the inward-facing surface 232 of the substrate 230 such that the bio-interactive electronics 260 are facing the concave surface 226 and able to receive urea concentrations from the inner tear film 40.

Bio-interactive electronics 260 can be made selectively sensitive to urea by localizing a reagent which selectively reacts with urea near the bio-interactive electronics 260. As shown in FIG. 2D, a reagent layer 261 can be located proximate to the bio-interactive electronics 260. The reagent layer 261 can be permeable to urea and contain reagents which selectively react with urea to create analytes which can be sensed directly by the bio-interactive electronics 260. In some examples, the reagent layer 261 is comprised of a nano-powder of zinc oxide and contains a reagent which selectively reacts with urea comprising urease. Urea from the outer tear layer 42 diffuses through the channel 272 to react selectively with the urease in the reagent layer 261; this reaction creates products including ammonia which can be detected potentiometrically by the zinc oxide nano-powder on a working electrode which is part of the bio-interactive electronics 260. Other chemical compositions can be used to comprise the reagent layer 261, and other urea-selective reagents can be disposed within the reagent layer 261, than have been disclosed above. For example, iridium oxide could be used in place of zinc oxide to detect the pH change which occurs near the reagent layer 261 due to the generation of ammonia in the reagent layer 261 by the decomposition of urea by urease. A protective layer 263 which is permeable to urea can be disposed on the reagent layer 261. The protective layer 263 can be composed of a polymer that is permeable to urea. The polymer may be formulated to include porogens to tailor the permeability to urea of the protective layer 263 for a specific application.

III. A Body-Mountable Electrochemical Urea Sensor

Figure 3:
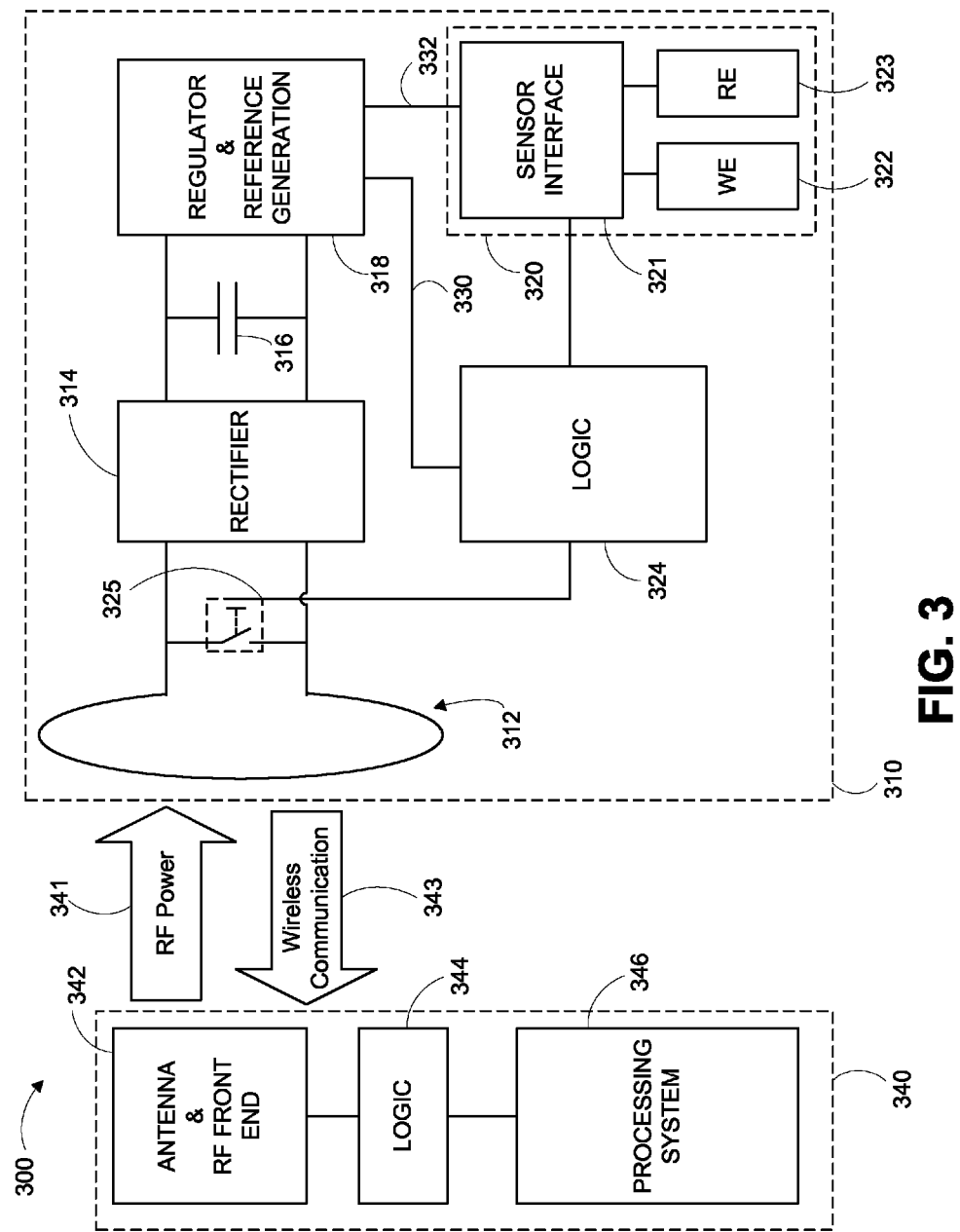
FIG. 3 is a functional block diagram of an example system for electrochemically measuring a urea concentration in a fluid.

FIG. 3 is a functional block diagram of a system 300 for electrochemically measuring a urea concentration in a fluid. The system 300 includes a body-mountable device 310 with embedded electronic components powered by an external reader 340. The body-mountable device 310 includes an antenna 312 for capturing radio frequency radiation 341 from the external reader 340. The body-mountable device 310 includes a rectifier 314, an energy storage element 316, and a regulator 318 for generating power supply voltages 330, 332 to operate the embedded electronics. The body-mountable device 310 includes an electrochemical sensor 320 with a working electrode 322 and a reference electrode 323 driven by a sensor interface 321. The body-mountable device 310 includes hardware logic 324 for communicating results from the sensor 320 to the external reader 340 by modulating (by means of modulation electronics and interconnects 325) the impedance of the antenna 312. Similar to the eye-mountable devices 110, 210 discussed above in connection with FIGS. 1 and 2, the body-mountable device 310 can include a mounting substrate embedded within a polymeric material configured to be mounted to an eye. The electrochemical sensor 320 can be situated on a mounting surface of such a substrate distal to the surface of the eye (e.g., corresponding to the bio-interactive electronics 260 on the outward-facing side 234 of the substrate 230) to measure analyte concentration in a tear film layer coating the exposed surface of the body-mountable device 310 on the eye (e.g., the outer tear film layer 42 interposed between the convex surface 224 of the polymeric material 210 and the atmosphere and/or closed eyelids). Alternatively, the electrochemical sensor 320 can be situated on a mounting surface of such a substrate proximal to the surface of the eye (e.g., on the inward-facing side 232 of the substrate 230) to measure urea concentration in a tear film layer interposed between the body-mountable device 310 and the eye (e.g., the inner tear film layer 40 between the eye-mountable device 210 and the corneal surface 22).

With reference to FIG. 3, the electrochemical sensor 320 measures urea concentration by measuring a potentiometric voltage between the electrodes 322, 323 that is caused by products of a reaction of the analyte catalyzed by the reagent at the working electrode 322. The sensor interface 321 measures the potentiometric voltage and provides an output to the hardware logic 324. The sensor interface 321 can include, for example, a high-impedance voltmeter connected to both electrodes 322, 323 to measure the equilibrium potentiometric voltage between the working electrode 322 and the reference electrode 323.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage element 316 (e.g., capacitor) is connected across the output of the rectifier 314 to filter high frequency noise on the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to operate a high-impedance voltmeter connected to the sensor electrodes 322, 323 to measure a potentiometric voltage. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to measure a potentiometric voltage and communicate the results.

The sensor results can be communicated back to the external reader 340 via backscatter radiation 343 from the antenna 312. The hardware logic 324 receives the output voltage from the electrochemical sensor 320 and modulates (325) the impedance of the antenna 312 in accordance with the potentiometric voltage measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or a network-connected memory. Alternatively, the sensor results can be communicated back to the external reader 340 via an internally generated radio frequency signal 343 from the antenna 312.

In some embodiments, one or more of the features shown as separate functional blocks can be implemented ("packaged") on a single chip. For example, the body-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, measure a potentiometric voltage between the electrodes 322, 323, and indicate the measured voltage via the antenna 312 (e.g., through backscatter radiation 343).

IV. Example Electrochemical Urea Sensor

Figure 4A:
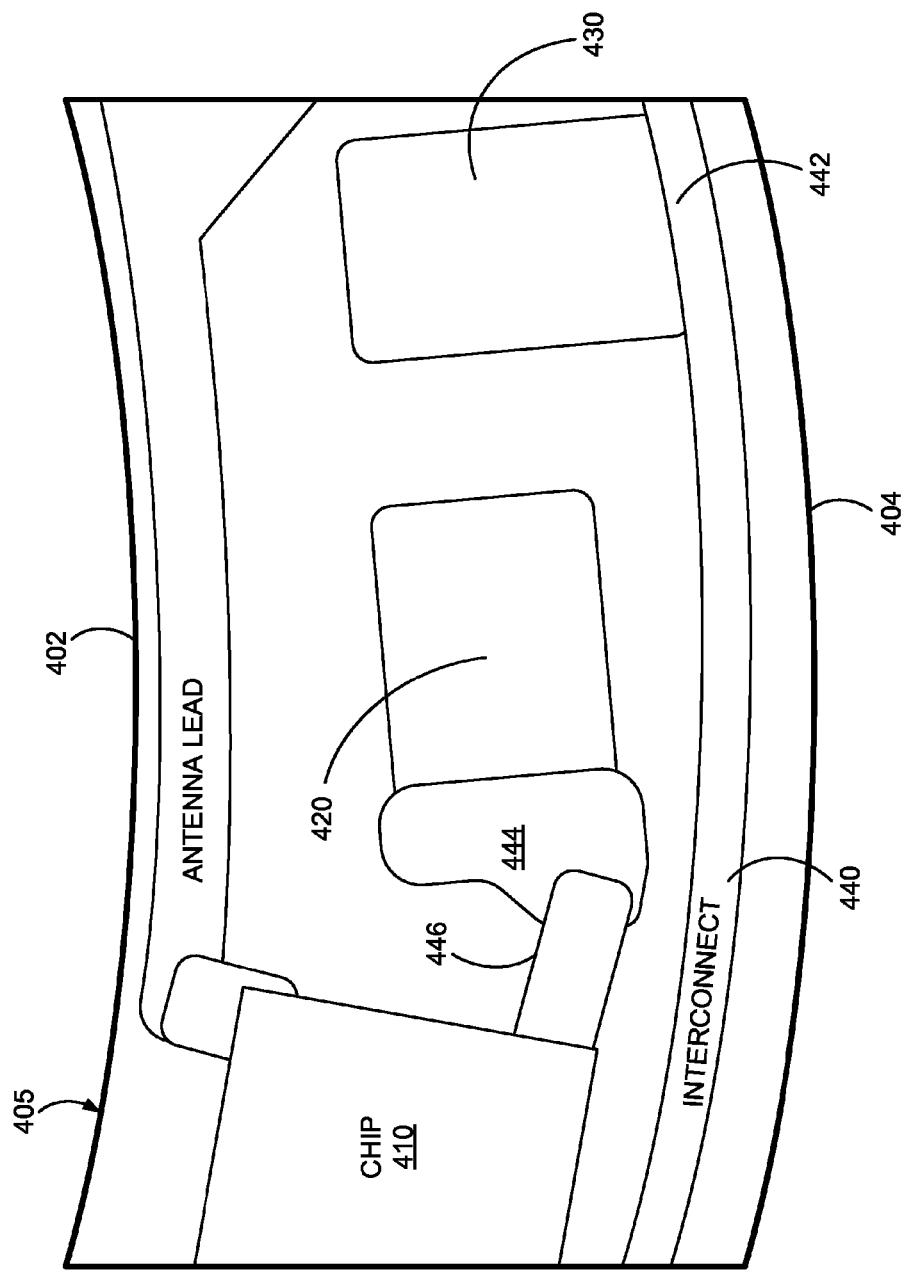
FIG. 4A illustrates an example arrangement for electrodes in an electrochemical urea sensor disposed on a surface of a flattened ring substrate.

FIG. 4A illustrates an example arrangement for electrodes in an electrochemical urea sensor disposed on a surface of a flattened ring substrate. FIG. 4A illustrates a portion of a substrate 405 on which an electrochemical urea sensor is mounted. The substrate 405 is configured to be embedded in an eye-mountable device and can be similar to the substrate 220 described above in connection with FIG. 2. The substrate 405 can be shaped as a flattened ring with an inner edge 402 and an outer edge 404. The two edges 402, 404 may both be at least approximately circular, although only a portion of each is shown in FIG. 4A.

The substrate 405 provides a mounting surface for mounting a chip 410 and for patterning sensor electrodes, an antenna, and conductive interconnects between pads or terminals on the chip 410 and the other components. An electrochemical urea sensor includes a working electrode 420 and a reference electrode 430 patterned on the substrate 405. The working electrode 420 is electrically connected to a connection pad of the chip 410 through a pair of overlapped interconnects 444, 446. The reference electrode 430 can then be electrically connected to another pad (not visible) on the chip 410 via the interconnect 440 that connects to the reference electrode 430 at multiple overlap points 442.

The chip 410 can also be connected to other components via additional connection pads. For example, as shown in FIG. 4A, the chip 410 can be connected to an antenna lead, which can be formed of a patterned conductive material, such as electroplated gold, for example, that substantially circles the substrate 405 to create a loop antenna.

Figure 4B:
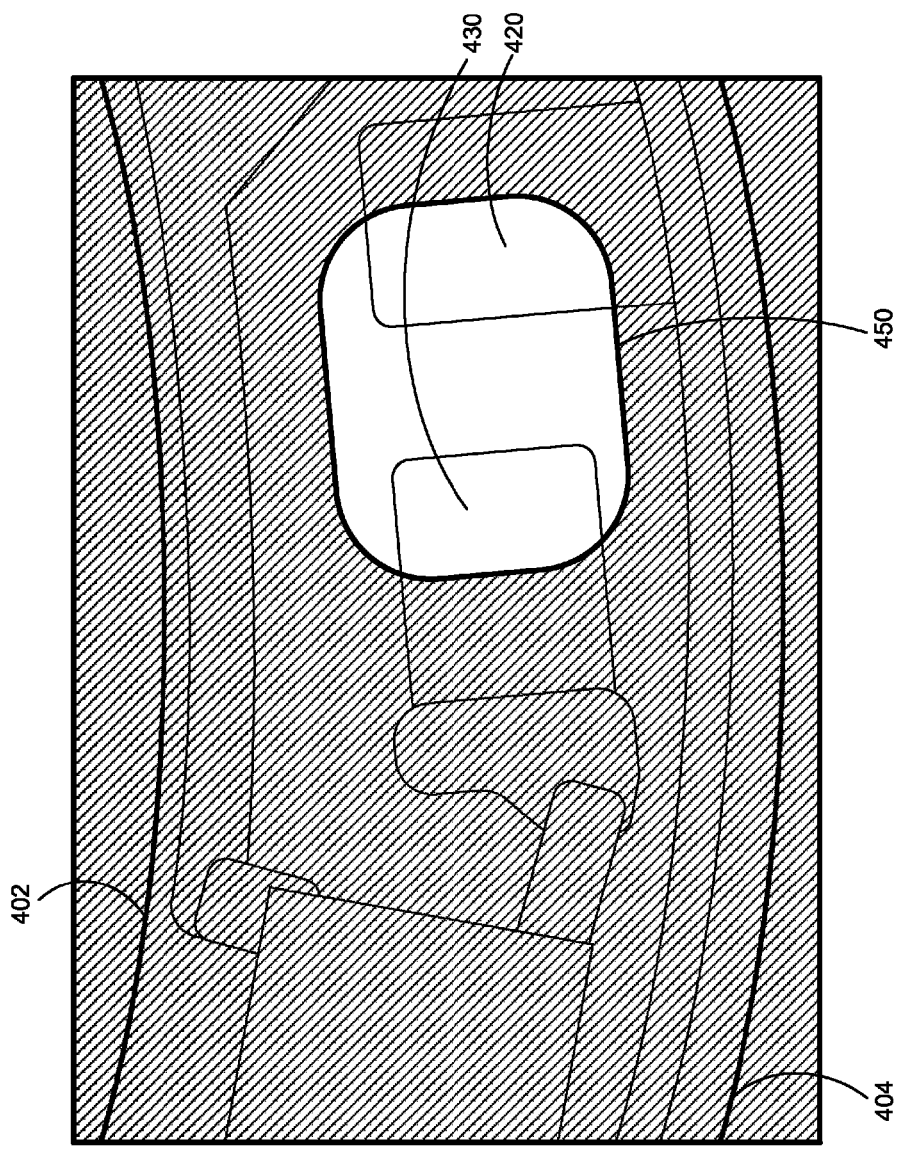
FIG. 4B illustrates the arrangement in FIG. 4A when embedded in a polymeric material with a channel positioned to expose the electrochemical urea sensor electrodes.

FIG. 4B illustrates the arrangement in FIG. 4A when embedded in a polymeric material with a channel 450 positioned to expose the electrochemical sensor electrodes 420, 430. In FIG. 4B, the polymeric material is illustrated by the hash pattern that is superimposed over the portion of the substrate 405 shown in FIG. 4A. The channel 450 may be formed by removing a portion of the encapsulating polymeric material (e.g., by etching, by removing a layer defined by a photoresist, etc.). The channel 450 exposes a region including the sensor electrodes 420, 430, such that tear film coating the polymeric material is able to contact the sensor electrodes 420, 430, and an analyte therein is able to electrochemically react at the electrodes.

While not specifically illustrated in FIG. 4A-4B, the electrochemical sensor may also include a reagent layer that immobilizes a suitable reagent near the working electrode 420 so as to sensitize the electrochemical sensor to urea. In some examples, this reagent layer takes the form of a nano-powder of a pH-sensitive material disposed on the working electrode 420 in the channel 450 positioned to expose the electrochemical sensor electrodes 420, 430 to a tear film. The nano-powder can be composed of zinc oxide, iridium oxide, or another pH-sensitive material. The reagent localized within the reagent layer can be comprised of urease. The urease can react with urea in the tear film to which the sensor electrodes 420, 430 are exposed, creating at least ammonia. The reagent can be localized within the reagent layer by being adsorbed or otherwise bonded to the surface of the particles of the nano-powder disposed on the working electrode 420. In some examples, the working electrode 420 comprises platinum and the reference electrode 430 comprises silver/silver chloride. The embodiments above are meant only as illustrative examples; other reagent layer compositions, urease-selective reagents, electrode materials, and nano-powder compositions are anticipated.

Figure 5:
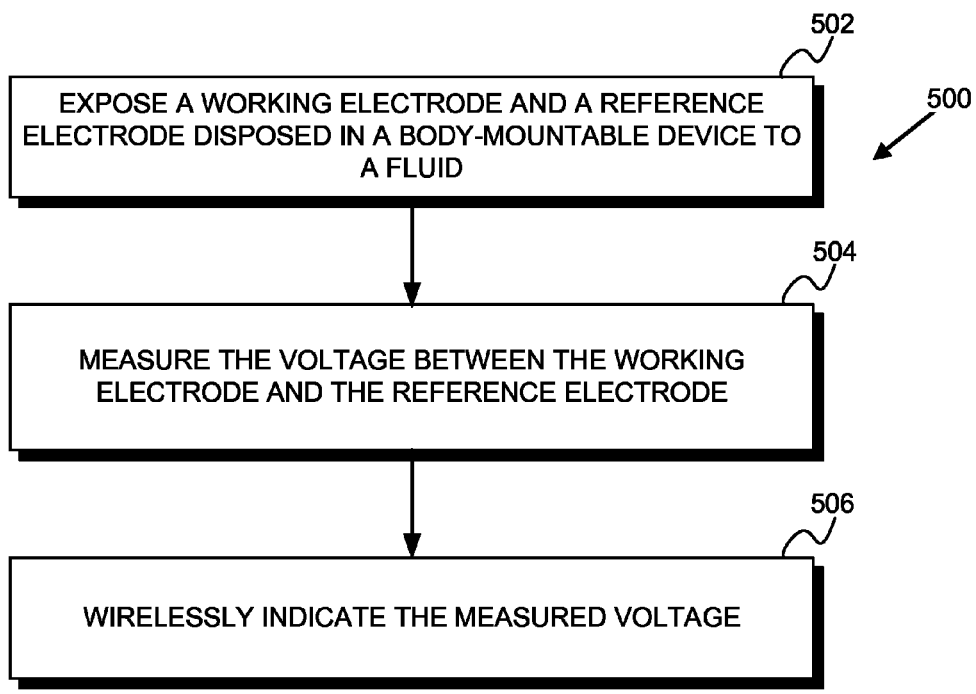
FIG. 5 is a flowchart of an example process for operating a potentiometric urea sensor in a body-mountable device to measure a urea concentration in a fluid.

Moreover, it is particularly noted that while the electrochemical urea sensor platform is described herein by way of example as an eye-mountable device or an ophthalmic device, it is noted that the disclosed electrochemical urea sensor and electrode arrangements therefore can be applied in other contexts as well. For example, electrochemical urea sensors disclosed herein may be included in wearable (e.g., body-mountable) and/or implantable potentiometric urea sensors. In some contexts, an electrochemical urea sensor is situated to be substantially encapsulated by bio-compatible polymeric material suitable for being in contact with bodily fluids and/or for being implanted. In one example, a mouth-mountable device includes an electrochemical urea sensor and is configured to be mounted within an oral environment, such as adjacent a tooth or adhered to an inner mouth surface. In another example, an implantable medical device that includes an electrochemical urea sensor may be encapsulated in biocompatible material and implanted within a host organism. Such body-mounted and/or implanted electrochemical urea sensors can include circuitry configured to operate a potentiometric sensor by measuring a voltage across sensor electrodes. The electrochemical urea sensor can also include an energy harvesting system and a communication system for wirelessly indicating the sensor results (i.e., measured voltage). In other examples, electrochemical urea sensors disclosed herein may be included in wireless potentiometric urea sensors which are not used to measure a urea concentration in or on a human body. For example, electrochemical urea sensors disclosed herein may be included in body-mountable and/or implantable potentiometric urea sensors used to measure a urea concentration in a fluid of an animal. In another example, electrochemical urea sensors disclosed herein may be included in devices to measure a urea concentration in an environmental fluid, such as a fluid in a river, lake, marsh, reservoir, water supply, sanitary sewer system, or storm sewer system. In another example, electrochemical urea sensors disclosed herein may be included in devices to measure a urea concentration in a fluid which is part of a process, such as a waste treatment process, pharmaceutical synthesis process, food preparation process, fermentation process, or medical treatment process V. Example Processes for Measuring Urea Concentration in a Fluid FIG. 5 is a flowchart of a process 500 for operating a potentiometric electrochemical urea sensor in a body-mountable device to measure a urea concentration in a fluid of a body. The body-mountable device is mounted on the body such that a working electrode and a reference electrode of the device are exposed to a fluid of the body (502). For example, the body-mountable device could be formed to substantially conform to a cornea of an eye of the body, and the device could be mounted on the cornea such that the working electrode and reference electrode of the device are exposed to a tear film of the eye. A potentiometric voltage is measured between the working electrode and the reference electrode on the electrochemical sensor (504). For example, a high-impedance voltmeter can measure a voltage between the working and reference electrodes while substantially preventing the flow of current through the working and reference electrodes. In an example embodiment, the working electrode can be a platinum electrode and the reference electrode can be a silver/silver chloride electrode, and a reagent that selectively reacts with urea to create at least ammonium hydroxide can be localized proximate to the working electrode. The measured potentiometric voltage is wirelessly indicated (506). For example, backscatter radiation can be manipulated to indicate the sensor result by modulating an impedance of an antenna.

Figure 6:
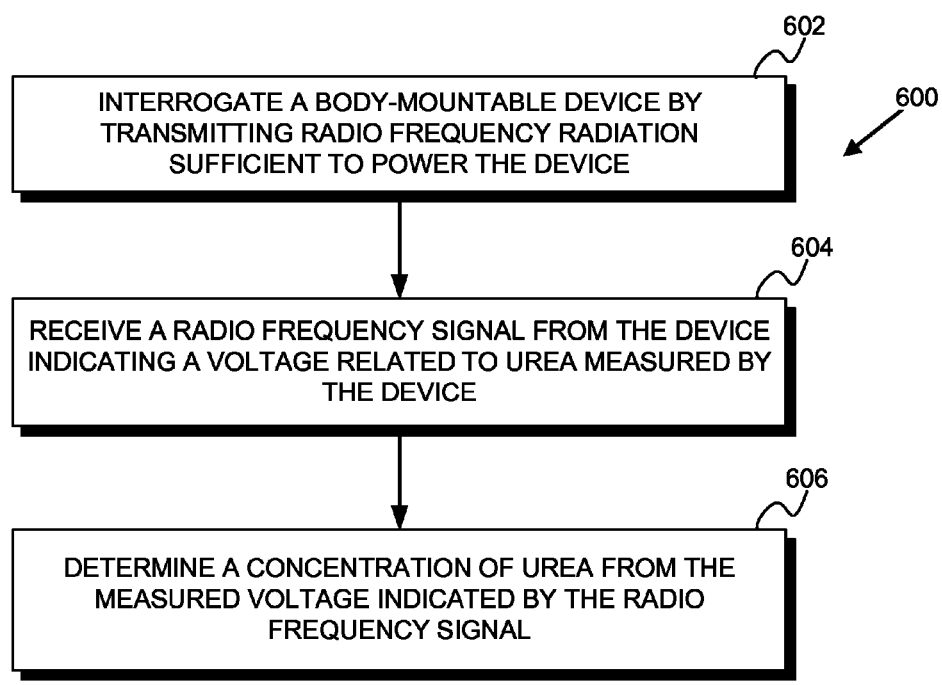
FIG. 6 is a flowchart of an example process for operating a system to interrogate a potentiometric urea sensor in a body-mountable device to measure a urea concentration in a fluid.

FIG. 6 is a flowchart of a process 600 for operating an external reader to interrogate a ptentiometric electrochemical urea sensor in a body-mountable device to measure a urea concentration of a fluid that the device is exposed to. Radio frequency radiation is transmitted to a body-mountable device from the external reader (602). The transmitted radiation is sufficient to power the electrochemical urea sensor with energy from the radiation for long enough to perform a measurement of urea concentration and communicate the results (602). For example, the radio frequency radiation used to power the electrochemical urea sensor can be similar to the radiation 341 transmitted from the external reader 340 to the body-mountable device 310 described in connection with FIG. 3 above. The external reader then receives a radio frequency signal from the body-mountable device indicating the measurement by the electrochemical urea sensor (604). For example, the radio frequency signal could be backscatter radiation similar to the backscatter signals 343 sent from the body-mountable device 310 to the external reader 340 described in connection with FIG. 3 above. The backscatter radiation received at the external reader is then associated with a fluid urea concentration (606). In some cases, the urea concentration values can be stored in the external reader memory (e.g., in the processing system 346) and/or a network-connected data storage. In some cases, the urea concentration value can be indicated on a display of the reader device. In some cases, the urea concentration may be measured at a plurality of points in time.

For example, the sensor result (e.g., the measured potentiometric voltage) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the body-mountable device. Thus, the reader can map a detected antenna impedance value to a potentiometric voltage value. The potentiometric voltage value is approximately proportionate to fluid urea concentration with a sensitivity (e.g., scaling factor) relating the potentiometric voltage and the associated fluid urea concentration. This urea concentration could then be indicated to a user of the reader by displaying the measured urea concentration on a display disposed on the reader. The sensitivity value can be determined in part according to empirically derived calibration factors, for example.

VI. Example Method for Fabricating a Body-Mountable Urea Sensor

Figure 7:
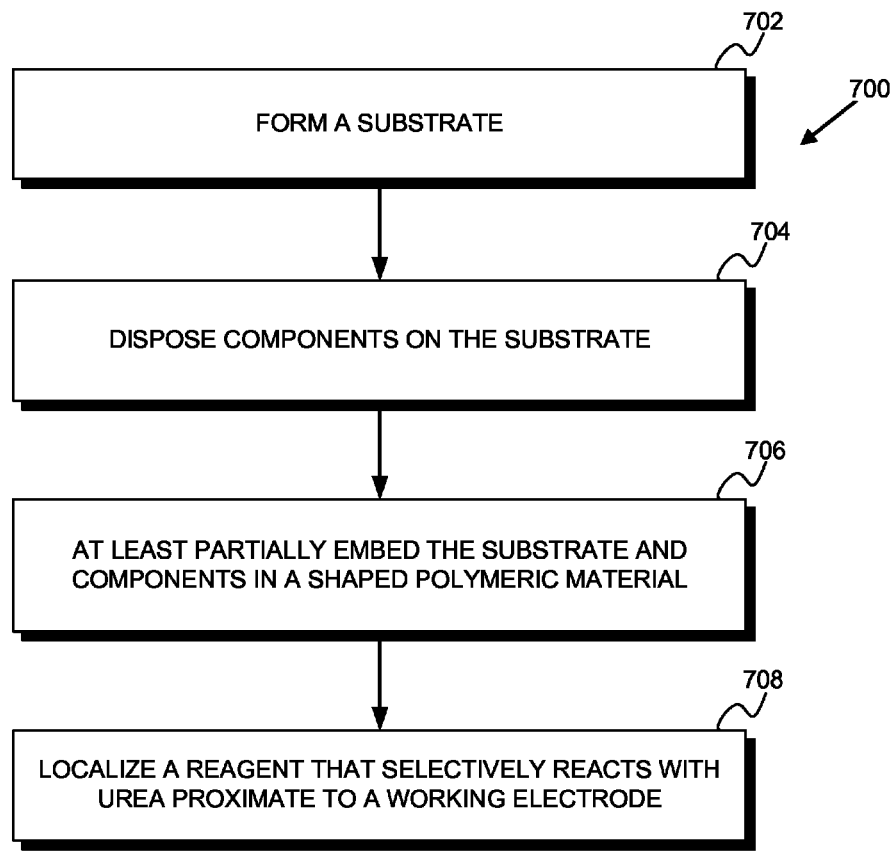
FIG. 7 is a flowchart of an example process for fabricating a body-mountable device capable of potentiometrically measuring a urea concentration in a fluid.

FIG. 7 is a flowchart of an example process 700 for fabricating a body-mountable device capable of potentiometrically measuring a urea concentration in a fluid. A substrate is formed (702) to provide a base structure for the fabrication of the device. The substrate can be a relatively rigid material, such as polyethylene terephthalate ("PET"), parylene, or another material configured to structurally support electrical components of an electrochemical urea sensor within a shaped polymeric material. In examples where the body-mountable device is mounted to a cornea of an eye, the substrate may be shaped as a flattened ring with a radial width dimension sufficient to provide a mounting platform for embedded electronics components. The substrate can optionally be aligned with a curvature of the cornea of the eye (e.g., convex surface). For example, the substrate can be shaped along the surface of an imaginary cone between two circular segments that define an inner radius and an outer radius. In such an example, the surface of the substrate along the surface of the imaginary cone defines an inclined surface that is approximately aligned with the curvature of the eye mounting surface at that radius. When the device is mounted to the eye, this example substrate does not interfere with vision because it is too close to the eye to be in focus and is positioned away from the central region where incident light is transmitted to the eye-sensing portions of the eye. Other materials and shapes of the substrate are anticipated according to applications of a body-mountable ures sensing device. The substrate may be formed into a single piece or multiple pieces later embedded in a single shaped polymeric material to form the body-mountable device.

Components are disposed on the substrate (704). Components may include loop antennas, electronic components, interconnects, and electrodes. The interconnects, loop antennas, and electrodes can be formed from conductive materials patterned on the substrate by a process for precisely patterning such materials, such as deposition, photolithography, etc. The conductive materials patterned on the substrate can be, for example, gold, platinum, palladium, titanium, carbon, aluminum, copper, silver, silver-chloride, conductors formed from noble materials, metals, combinations of these, etc. In some embodiments, some electronic components can be mounted on one side of the substrate, while other electronic components are mounted to the opposing side, and connections between the two can be made through conductive materials passing through the substrate. Components such as electronic chips may be disposed on the substrate and connected to the other components by methods familiar to one skilled in the art (e.g., pick-and-place machines, flip-chip mounting). The components include at least a working electrode and a reference electrode which can be configured to sense the concentration of urea in a fluid to which the body-mountable device is exposed. The electrodes can be disposed on the substrate as described above.

The substrate and components disposed thereon are at least partially embedded in a shaped polymeric material (706). In examples where the body-mountable device is mounted to a cornea of an eye, the shaped polymeric material can be shaped as a curved disk. The polymeric material can be a substantially transparent material to allow incident light to be transmitted to the eye while the body-mountable device is mounted to the eye. The polymeric material can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, combinations of these, etc. The polymeric material can be formed with one side having a concave surface suitable to fit over a corneal surface of an eye. The opposite side of the disk can have a convex surface that does not interfere with eyelid motion while the body-mountable device is mounted to the eye. In some embodiments, the dimensions of the shaped polymeric material of the body-mountable device can be selected according to the size and/or shape of the corneal surface of a wearer's eye.

The polymeric material can be formed in a variety of ways. For example, techniques similar to those employed to form vision-correction contact lenses, such as heat molding, injection molding, spin casting, etc. can be employed to form the shaped polymeric material. In examples where the shaped polymeric material is shaped to be mounted to a cornea of an eye the substrate and components disposed thereon can be embedded to be situated along the outer periphery of the curved disk shape of the polymeric material, away from a central region. The substrate and components disposed thereon do not interfere with vision because they are too close to the eye to be in focus and are positioned away from the central region where incident light is transmitted to the eye-sensing portions of the eye. Moreover, the substrate can be formed of a transparent material to further mitigate effects on visual perception. Partially embedding the substrate and components disposed thereon can mean covering the substrate and components thereon except for a working electrode and reference electrode of an electrochemical urea sensor, so that only the working electrode and reference electrode of the urea sensor are in direct contact with the fluid to which the body-mountable device is exposed. In some embodiments, other components or parts of the substrate are not covered by the shaped polymeric material. For example, more than one electrochemical sensor may be disposed on the substrate, and the electrodes associated with the more than one sensor may not be covered by the shaped polymeric material.

A reagent that selectively reacts with urea is localized proximate to a working electrode disposed on the substrate (708). In some examples, a solution including urea-selective reagents, a pH-sensitive metal oxide nano-powder, water, and alcohol is synthesized, applied to the working electrode, and the water and alcohol are evaporated leaving the particles of the nano-powder disposed on the working electrode and the urea-selective reagent adsorbed on the particles of the nano-powder. The urea-selective reagent can include urease. The pH-sensitive metal oxide can include zinc oxide, iridium oxide, tin oxide, cerium oxide, or other materials or combinations of materials. Other solutions are anticipated, wherein different pH-sensitive materials, aqueous or non-aqueous solvents, or urea-selective reagents are used according to the application of fabricating a body-mountable device to detect urea concentration in a fluid. For example, the pH-sensitive metal oxide may take the form of nanowires or may be coated on the surface of the working electrode by plating, deposition, or some other method. A protective layer can be formed over the urea-selective reagent layer. This layer can be composed of a urea-permeable polymer or some other material which is permeable to urea and which can be deposited on the reagent layer while leaving the ability of the reagent layer to detect urea substantially intact.

CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

Further, where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

In situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from a content server that may be more relevant to the user. In addition, certain data may be treated in one or more ways before it is stored or used, so that personally identifiable information is removed. For example, a user's identity may be treated so that no personally identifiable information can be determined for the user. Thus, the user may have control over how information is collected about the user and used by a content server.

What is claimed is:

1. A body-mountable device comprising:
   a shaped polymeric material having a channel formed therein;
   a substrate at least partially embedded within the shaped polymeric material and adjacent to the channel;
   an antenna disposed on the substrate;
   an electrochemical sensor disposed on the substrate and comprising:
      a working electrode;
      a protective layer comprising a polymer permeable to urea;
      a reagent that selectively reacts with urea, wherein the reagent is localized within a reagent layer disposed in the channel between the protective layer and the working electrode; and
      a reference electrode; and
   a controller disposed on the substrate and embedded within the shaped polymeric material, wherein the controller is electrically connected to the electrochemical sensor and the antenna, wherein the controller is configured to: (i) measure a potentiometric voltage between the working electrode and the reference electrode related to the concentration of urea in a fluid to which the body-mountable device is exposed; and (iii) use the antenna to indicate the measured potentiometric voltage.

2. The body-mountable device according to claim 1, wherein the fluid is a tear fluid of an eye, wherein the shaped polymeric material has a concave surface and a convex surface, wherein the concave surface is configured to be removably mounted over a corneal surface and the convex surface is configured to be compatible with eyelid motion when the concave surface is so mounted.

3. The body-mountable device according to claim 1, wherein the reagent layer comprises a pH-responsive oxide.

4. The body-mountable device according to claim 3, wherein the pH-responsive oxide is in the form of a nano-powder, wherein the reagent that selectively reacts with urea is disposed on the particles of the nano-powder.

5. The body-mountable device according to claim 3, wherein the pH-responsive oxide includes zinc oxide.

6. The body-mountable device according to claim 3, wherein the pH-responsive oxide includes iridium oxide.

7. The body-mountable device according to claim 1, wherein the reagent comprises urease.

8. The body-mountable device according to claim 1, wherein the working electrode comprises platinum and the reference electrode comprises silver/silver-chloride.

9. The body-mountable device according to claim 1, wherein the antenna is configured to receive radio frequency energy to power the body-mountable device.

10. The body-mountable device according to claim 1, wherein using the antenna to indicate the measured potentiometric voltage comprises sending a radio frequency signal.

11. The body-mountable device according to claim 1, wherein using the antenna to indicate the measured potentiometric voltage comprises reflecting a radio frequency signal.

12. A method comprising:
   exposing a working electrode and a reference electrode disposed in a body-mountable device to a fluid via a protective layer and a reagent layer disposed in a channel of the body-mountable device, wherein the protective layer comprises a polymer permeable to urea, wherein the reagent layer comprises a reagent that selectively reacts with urea, wherein the body-mountable device additionally includes an antenna and measurement electronics, and wherein the working electrode, reference electrode, antenna, and measurement electronics are disposed on a substrate that is at least partially embedded in a shaped polymeric material and adjacent to the channel;
   measuring, by a controller, a potentiometric voltage between the working electrode and the reference electrode related to the concentration of urea in a fluid to which the body-mountable device is exposed, wherein the controller is disposed on the substrate and embedded within the shaped polymeric material; and
   wirelessly indicating the measured voltage using the antenna.

13. The method of claim 12, wherein the fluid is a tear fluid of an eye, and wherein the shaped polymeric material has a concave surface and a convex surface, wherein the concave surface is configured to be removably mounted over a corneal surface of the eye and the convex surface is configured to be compatible with eyelid motion when the concave surface is so mounted.

14. The method of claim 12, wherein measuring the potentiometric voltage and wirelessly indicating the measured voltage using the antenna are performed in response to an interrogating radio frequency signal received by the antenna.

15. The method of claim 14, where the interrogating radio frequency signal is used to power the body-mountable device.

16. The method of claim 14, wherein wirelessly indicating the measured voltage comprises reflecting a version of the interrogating radio frequency signal.

17. The body-mountable device according to claim 12, wherein the reagent comprises urease.

18. The body-mountable device according to claim 12, wherein the reagent layer comprises zinc oxide.

19. The body-mountable device according to claim 12, wherein the reagent layer comprises iridium oxide.

* * * * *